United States Patent
Al Mutairy et al.

(10) Patent No.: US 11,992,515 B2
(45) Date of Patent: May 28, 2024

(54) METHOD FOR TREATING PULMONARY FIBROSIS USING S100A3 PROTEIN

(71) Applicant: KING FAISAL SPECIALIST HOSPITAL & RESEARCH CENTRE, Riyadh (SA)

(72) Inventors: Eid Abdullah Al Mutairy, Riyadh (SA); Mohammed Khalid, Riyadh (SA); Futwan Al-Mohanna, Riyadh (SA)

(73) Assignee: KING FAISAL SPECIALIST HOSPITAL & RESEARCH CENTRE, Riyadh (SA)

( * ) Notice: Subject to any disclaimer, the term of this patent is extended or adjusted under 35 U.S.C. 154(b) by 290 days.

(21) Appl. No.: 17/080,268

(22) Filed: Oct. 26, 2020

(65) Prior Publication Data

US 2021/0052700 A1    Feb. 25, 2021

Related U.S. Application Data

(63) Continuation of application No. 16/155,371, filed on Oct. 9, 2018, now abandoned.

(51) Int. Cl.
| | | |
|---|---|---|
| *A61P 11/00* | (2006.01) | |
| *A61K 9/00* | (2006.01) | |
| *A61K 38/00* | (2006.01) | |
| *A61K 38/17* | (2006.01) | |
| *A61P 9/04* | (2006.01) | |
| *A61P 11/08* | (2006.01) | |
| *C07K 14/47* | (2006.01) | |
| *C12N 15/52* | (2006.01) | |
| *C12Q 1/68* | (2018.01) | |
| *C12Q 1/6813* | (2018.01) | |
| *C12Q 1/6827* | (2018.01) | |

(52) U.S. Cl.
CPC ............ *A61K 38/1738* (2013.01); *A61P 9/04* (2018.01); *A61P 11/00* (2018.01); *C07K 14/4728* (2013.01); *C12N 15/52* (2013.01); *A61K 9/0073* (2013.01); *A61K 9/0075* (2013.01); *C12Q 1/6813* (2013.01); *C12Q 1/6827* (2013.01)

(58) Field of Classification Search
None
See application file for complete search history.

(56) References Cited

U.S. PATENT DOCUMENTS

| | | |
|---|---|---|
| 7,935,839 B2 | 5/2011 | Frincke |
| 9,404,926 B2 | 8/2016 | James et al. |
| 2017/0205429 A1 | 7/2017 | Figeys et al. |

FOREIGN PATENT DOCUMENTS

| | | |
|---|---|---|
| EP | 2 773 367 B1 | 9/2015 |
| EP | 2 550 359 B1 | 8/2017 |

OTHER PUBLICATIONS

Ying Liu, et al., "Prognostic Roles of mRNA Expression of S100 in Non-Small-Cell Lung Cancer", Biomed Research International, vol. 2018, Article ID 9815806, Jan. 21, 2018, 11 pages.
Tomasz Tyszkiewicz, et al., "Epidermal differentiation complex (locus 1q21) gene expression in head and neck cancer and normal mucosa", Folia Histochemica Et Cytobiologica, vol. 52, No. 2, 2014, pp. 79-89.
Ting Wang, et al, "A review of S100 protein family in lung cancer", Clinica Chimica Acta, vol. 476, 2018, pp. 54-59.
Steven K. Huang, et al., "Lung Fibroblasts from Patients with Idiopathic Pulmonary Fibrosis Exhibit Genome-Wide Differences in DNA Methylation Compared to Fibroblasts from Nonfibrotic Lung", Plos One, www.plosone.org, vol. 9, Issue 9, Sep. 2014, 15 pages.
R. Böni, et al., "Immunohistochemical localization of the Ca2+ binding S100 proteins in normal human skin and melanocytic lesions", British Journal of Dermatology, vol. 137, 1997, pp. 39-43.
Ibrahim Türkbeyler, et al., "Prolidase Could Act as a Diagnosis and Treatment Mediator in Lung Fibrosis", Inflammation, vol. 35, No. 5, Oct. 2012, pp. 1747-1752.
Monica J. Justice, et al., "Using the mouse to model human disease: increasing validity and reproducibility", Disease Models & Mechanisms, vol. 9, 2016, pp. 101-103.
Eid A. Al-Mutairy, et al., "An atypical pulmonary fibrosis is associated with co-inheritance of mutations in the calcium binding protein genes S100A3 and S100A13", Eur Respir J., vol. 54, No. 1802041, 2019, pp. 1-15.

*Primary Examiner* — Elizabeth C. Kemmerer
*Assistant Examiner* — Regina M DeBerry
(74) *Attorney, Agent, or Firm* — Oblon, McClelland, Maier & Neustadt, L.L.P.

(57) ABSTRACT

The invention is directed to a method for diagnosing and treating a pulmonary lung disease by detecting a mutant S100A3 protein associated with pulmonary lung disease and by treating a subject with a functional S100A3 protein.

7 Claims, 7 Drawing Sheets

Specification includes a Sequence Listing.

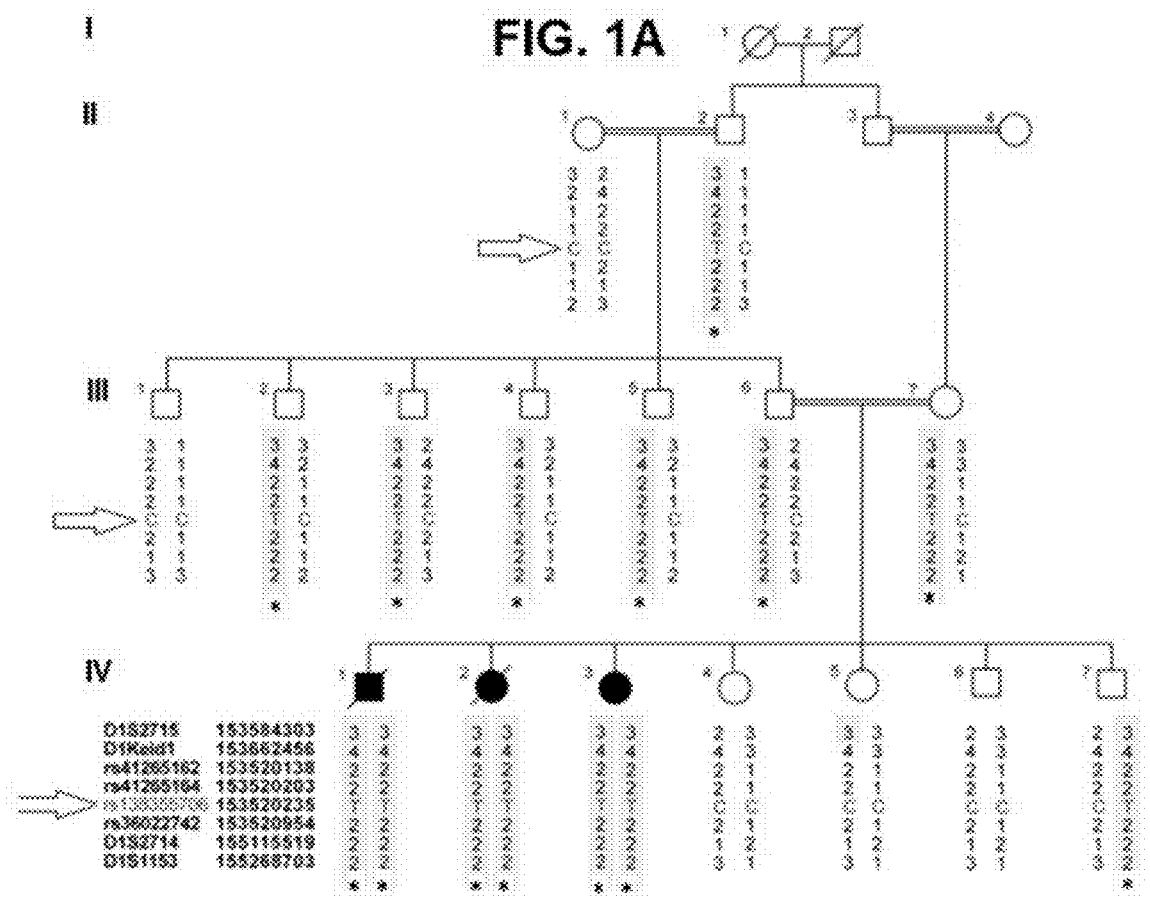
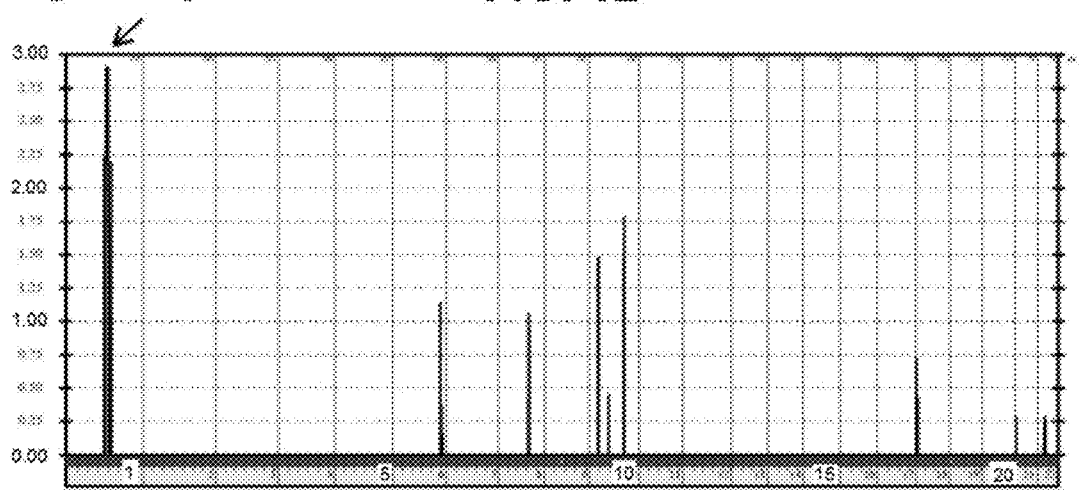

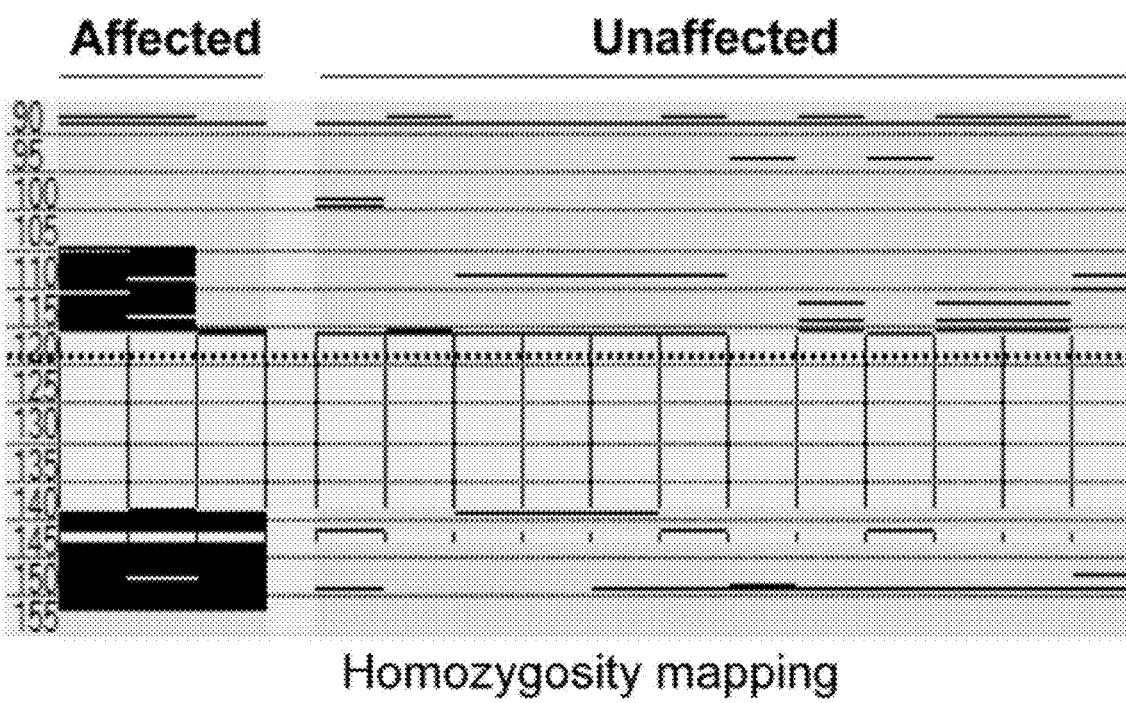

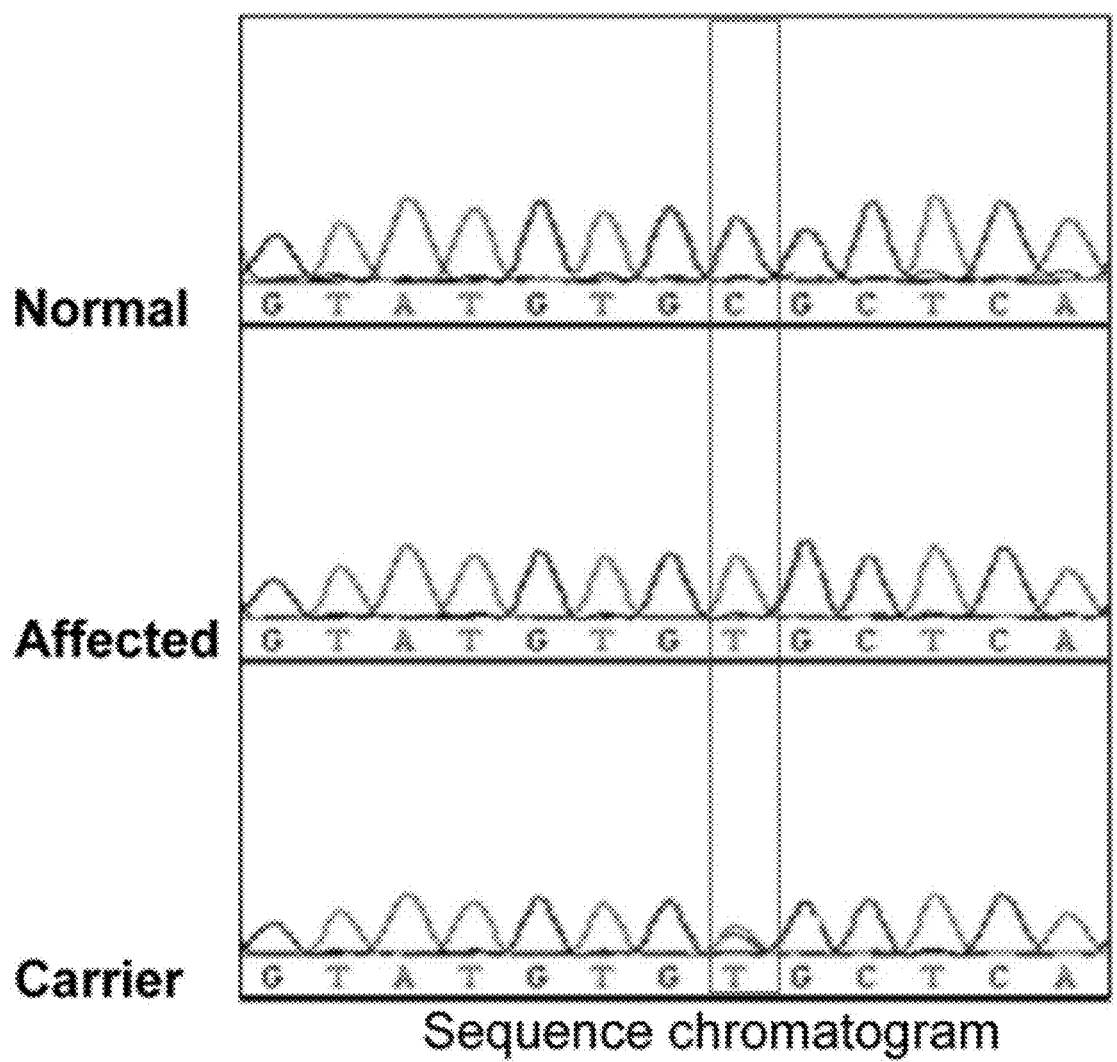

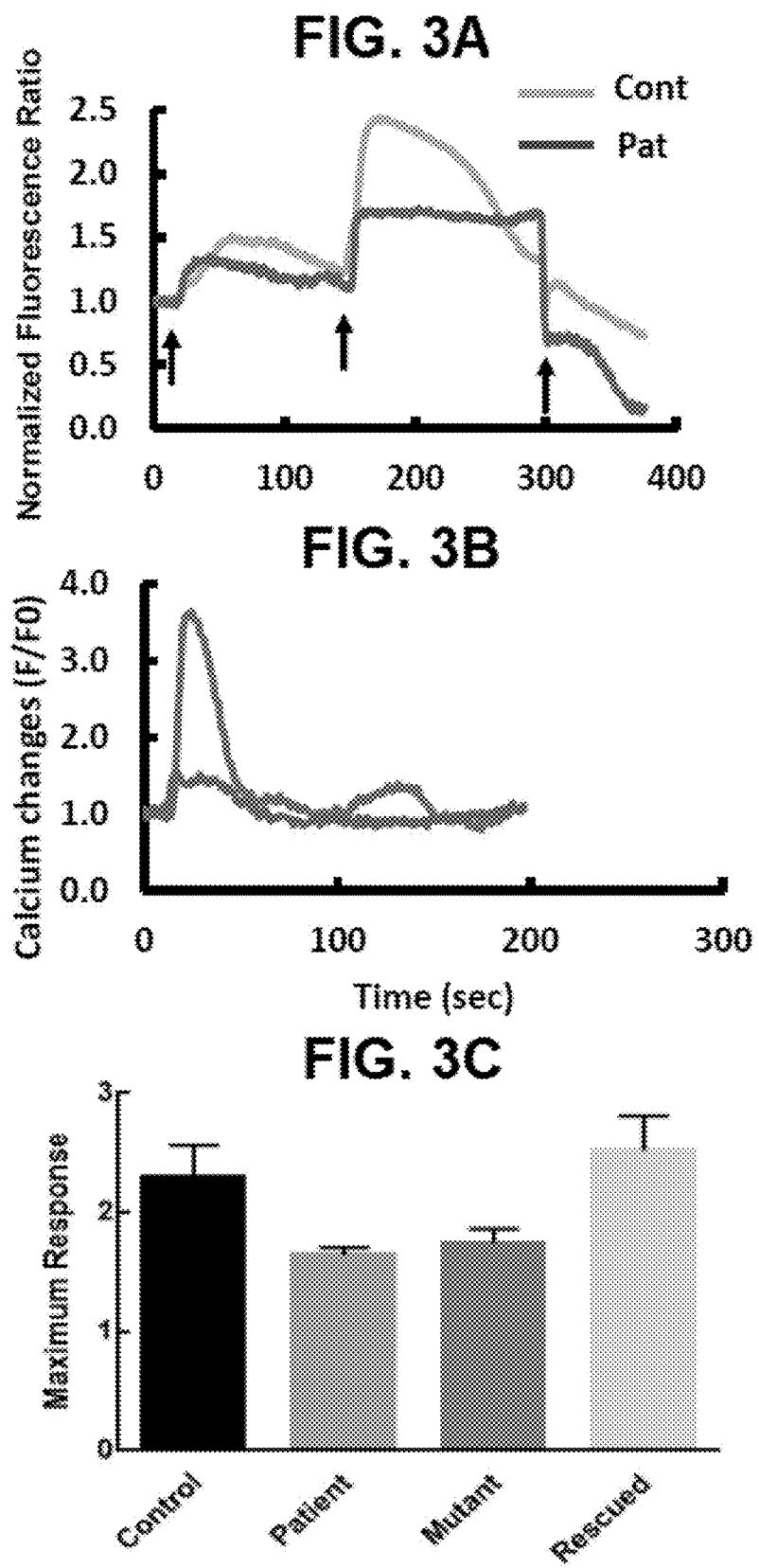

Control

Patient

… (1)

SEQUENCE LISTING

```
<160> NUMBER OF SEQ ID NOS: 12

<210> SEQ ID NO 1
<211> LENGTH: 738
<212> TYPE: DNA
<213> ORGANISM: Homo sapiens
<220> FEATURE:
<221> NAME/KEY: misc_feature
<222> LOCATION: (4)..(90)
<223> OTHER INFORMATION: Dimerization interface:
      order(4..20,26..28,37..38,40..42,70..73,75..76,78..81, 83..90)
<220> FEATURE:
<221> NAME/KEY: misc_feature
<222> LOCATION: (20)..(74)
<223> OTHER INFORMATION: Ca2+ binding site: order (20,25,28,33..34,63,
      65,67,69,71,74)
<220> FEATURE:
<221> NAME/KEY: CDS
<222> LOCATION: (84)..(389)

<400> SEQUENCE: 1
```

```
agtctcagat tggtaaacac ccgaactggt caactctcaa gagaccatct ggttcaggtt        60
cctgactggg ccagcgagtg agg atg gcc agg cct ctg gag cag gcg gta gct       113
                        Met Ala Arg Pro Leu Glu Gln Ala Val Ala
                          1               5                  10 gcc atc gtg tgc acc ttc cag gaa tac gca ggg cgc tgt ggg gac aaa         161
Ala Ile Val Cys Thr Phe Gln Glu Tyr Ala Gly Arg Cys Gly Asp Lys
                 15                  20                  25 tac aag ctc tgc cag gcg gag ctc aag gag ctg ctg cag aag gag ctg         209
Tyr Lys Leu Cys Gln Ala Glu Leu Lys Glu Leu Leu Gln Lys Glu Leu
         30                  35                  40 gcc acc tgg acc ccg act gag ttt cgg gaa tgt gac tac aac aaa ttc         257
Ala Thr Trp Thr Pro Thr Glu Phe Arg Glu Cys Asp Tyr Asn Lys Phe
     45                  50                  55 atg agt gtt ctg gac acc aac aag gac tgc gag gtg gac ttt gtg gag         305
Met Ser Val Leu Asp Thr Asn Lys Asp Cys Glu Val Asp Phe Val Glu
 60                  65                  70 tat gtg cgc tca ctt gcc tgc ctc tgt ctc tac tgc cac gag tac ttc         353
Tyr Val Arg Ser Leu Ala Cys Leu Cys Leu Tyr Cys His Glu Tyr Phe
 75                  80                  85                  90 aag gac tgc ccc tca gag ccc ccc tgc tcc cag tag cctctgctcc              399
Lys Asp Cys Pro Ser Glu Pro Pro Cys Ser Gln
                 95                 100 agggggtgcg ctggctgtcg ggggctgggc atgtctccca cacccctcc tacccctctc        459 cctgtacccc tttcaatctg gacttgccca ggtcttctgc gatcagttaa cccatttac        519 ctaggaggcc cagagatgtg agggctcctt cctcaggatg cccagcgaat gaggggtaga       579
gccactctgg ggcccagcct gcctgccgca cccctgtggc ctcccttgtg gatgggagga       639
ggcgggatct gctctgaggc cctcgaggct cagcagagcg tgcaccaatg agaccacgat       699
gggaaagggc ctatttaact cctaataaaa aactggcat                              738

<210> SEQ ID NO 2
<211> LENGTH: 101
<212> TYPE: PRT
<213> ORGANISM: Homo sapiens

<400> SEQUENCE: 2

Met Ala Arg Pro Leu Glu Gln Ala Val Ala Ala Ile Val Cys Thr Phe
  1               5                  10                  15

Gln Glu Tyr Ala Gly Arg Cys Gly Asp Lys Tyr Lys Leu Cys Gln Ala
                 20                  25                  30

Glu Leu Lys Glu Leu Leu Gln Lys Glu Leu Ala Thr Trp Thr Pro Thr
             35                  40                  45

Glu Phe Arg Glu Cys Asp Tyr Asn Lys Phe Met Ser Val Leu Asp Thr
         50                  55                  60

Asn Lys Asp Cys Glu Val Asp Phe Val Glu Tyr Val Arg Ser Leu Ala
 65                  70                  75                  80

Cys Leu Cys Leu Tyr Cys His Glu Tyr Phe Lys Asp Cys Pro Ser Glu
                 85                  90                  95

Pro Pro Cys Ser Gln
            100

<210> SEQ ID NO 3
<211> LENGTH: 720
<212> TYPE: DNA
<213> ORGANISM: Homo sapiens
<220> FEATURE:
<221> NAME/KEY: CDS
```

```
<222> LOCATION: (84)..(389)
<223> OTHER INFORMATION: Mutant rs138355706

<400> SEQUENCE: 3
agtctcagat tggtaaacac ccgaactggt caactctcaa gagaccatct ggttcaggtt      60
cctgactggg ccagcgagtg agg atg gcc agg cct ctg gag cag gcg gta gct     113
                         Met Ala Arg Pro Leu Glu Gln Ala Val Ala
                           1               5                  10 gcc atc gtg tgc acc ttc cag gaa tac gca ggg cgc tgt ggg gac aaa       161
Ala Ile Val Cys Thr Phe Gln Glu Tyr Ala Gly Arg Cys Gly Asp Lys
             15                  20                  25 tac aag ctc tgc cag gcg gag ctc aag gag ctg ctg cag aag gag ctg       209
Tyr Lys Leu Cys Gln Ala Glu Leu Lys Glu Leu Leu Gln Lys Glu Leu
         30                  35                  40 gcc acc tgg acc ccg act gag ttt cgg gaa tgt gac tac aac aaa ttc       257
Ala Thr Trp Thr Pro Thr Glu Phe Arg Glu Cys Asp Tyr Asn Lys Phe
     45                  50                  55 atg agt gtt ctg gac acc aac aag gac tgc gag gtg gac ttt gtg gag       305
Met Ser Val Leu Asp Thr Asn Lys Asp Cys Glu Val Asp Phe Val Glu
 60                  65                  70 tat gtg tgc tca ctt gcc tgc ctc tgt ctc tac tgc cac gag tac ttc       353
Tyr Val Cys Ser Leu Ala Cys Leu Cys Leu Tyr Cys His Glu Tyr Phe
 75                  80                  85                  90 aag gac tgc ccc tca gag ccc ccc tgc tcc cag tag cctctgctcc            399
Lys Asp Cys Pro Ser Glu Pro Pro Cys Ser Gln
                 95                 100 agggggtgcg ctggctgtcg ggggctgggc atgtctccca cacccctcc tacccctctct     459 cctgtacccc tttcaatctg gacttgccca ggtcttctgc gatcagttaa cccattttac     519
ctaggaggcc cagagatgtg agggctcctt cctcaggatg cccagcgaat gaggggtaga     579
gccactctgg ggcccagcct gcctgccgca ccccctgtggc ctcccttgtg gatgggagga    639
ggcgggatct gctctgaggc cctcgaggct cagcagagcg tgcaccaatg agaccacgat     699
gggaaagggc ctatttaact c                                              720

<210> SEQ ID NO 4
<211> LENGTH: 101
<212> TYPE: PRT
<213> ORGANISM: Homo sapiens

<400> SEQUENCE: 4

Met Ala Arg Pro Leu Glu Gln Ala Val Ala Ile Val Cys Thr Phe
  1               5                  10                  15

Gln Glu Tyr Ala Gly Arg Cys Gly Asp Lys Tyr Lys Leu Cys Gln Ala
                 20                  25                  30

Glu Leu Lys Glu Leu Leu Gln Lys Glu Leu Ala Thr Trp Thr Pro Thr
             35                  40                  45

Glu Phe Arg Glu Cys Asp Tyr Asn Lys Phe Met Ser Val Leu Asp Thr
         50                  55                  60

Asn Lys Asp Cys Glu Val Asp Phe Val Glu Tyr Val Cys Ser Leu Ala
 65                  70                  75                  80

Cys Leu Cys Leu Tyr Cys His Glu Tyr Phe Lys Asp Cys Pro Ser Glu
                 85                  90                  95

Pro Pro Cys Ser Gln
                100

<210> SEQ ID NO 5
<211> LENGTH: 20
```

```
<212> TYPE: DNA
<213> ORGANISM: Artificial Sequence
<220> FEATURE:
<223> OTHER INFORMATION: S100A3 forward primer

<400> SEQUENCE: 5
cccgaactgg tcaactctca                                               20

<210> SEQ ID NO 6
<211> LENGTH: 20
<212> TYPE: DNA
<213> ORGANISM: Artificial Sequence
<220> FEATURE:
<223> OTHER INFORMATION: S100A3 reverse primer

<400> SEQUENCE: 6
gcctggcaga gcttgtattt                                               20

<210> SEQ ID NO 7
<211> LENGTH: 20
<212> TYPE: DNA
<213> ORGANISM: Artificial Sequence
<220> FEATURE:
<223> OTHER INFORMATION: Plasmid backbone primer forward

<400> SEQUENCE: 7
gtggcgcttt ctcatagctc                                               20

<210> SEQ ID NO 8
<211> LENGTH: 20
<212> TYPE: DNA
<213> ORGANISM: Artificial Sequence
<220> FEATURE:
<223> OTHER INFORMATION: tgtcttaccgggttggactc

<400> SEQUENCE: 8
tgtcttaccg ggttggactc                                               20

<210> SEQ ID NO 9
<211> LENGTH: 19
<212> TYPE: DNA
<213> ORGANISM: Artificial Sequence
<220> FEATURE:
<223> OTHER INFORMATION: qRT-PCR forward primer

<400> SEQUENCE: 9
ggaccccgac tgagtttcg                                                19

<210> SEQ ID NO 10
<211> LENGTH: 20
<212> TYPE: DNA
<213> ORGANISM: Artificial Sequence
<220> FEATURE:
<223> OTHER INFORMATION: qRT-PCR reverse primer

<400> SEQUENCE: 10
gctctgaggg gcagtccttg                                               20

<210> SEQ ID NO 11
<211> LENGTH: 20
<212> TYPE: DNA
<213> ORGANISM: Artificial Sequence
<220> FEATURE:
<223> OTHER INFORMATION: GAPDH control primer forward

<400> SEQUENCE: 11
```

```
caccatcttc caggagtgag                                                    20

<210> SEQ ID NO 12
<211> LENGTH: 20
<212> TYPE: DNA
<213> ORGANISM: Artificial Sequence
<220> FEATURE:
<223> OTHER INFORMATION: GAPDH control primer reverse

<400> SEQUENCE: 12
tcacgccaca gtttcccgga                                                    20
```

METHOD FOR TREATING PULMONARY FIBROSIS USING S100A3 PROTEIN

CROSS-REFERENCE TO RELATED APPLICATIONS

The present application is a continuation application of U.S. application Ser. No. 16/155,371, filed Oct. 9, 2018, the entire contents of which are incorporated herein by reference.

REFERENCE TO A SEQUENCE LISTING

In accordance with 37 CFR § 1.52(e)(5), the present specification makes reference to a Sequence Listing submitted electronically as a .txt file named "513629US_ST25.txt" on Oct. 9, 2018. The .txt file was generated on Sep. 19, 2018 and is 9 kb in size. The entire contents of the Sequence Listing are herein incorporated by reference.

BACKGROUND

Field of the Invention

The invention involves the fields of molecular genetics, diagnostic and therapeutic medicine, and pharmacology.

Description of Related Art

The "background" description provided herein is for the purpose of generally presenting a context for the disclosure. Work of the presently named inventor(s), to the extent it is described in this background section, as well as aspects of the description which may not otherwise qualify as prior art at the time of filing, are neither expressly or impliedly admitted as prior art against the present invention.

The Interstitial Lung Diseases (ILDs) are a heterogeneous group of disorders of largely unknown etiology. They are characterized by variable types of interstitial and alveolar inflammation, parenchymal remodeling, and fibrosis; Nogee L M. *Genetics of pediatric interstitial lung disease.* Current opinion in pediatrics 2006; 18:287-92. The most common form of ILD is idiopathic Pulmonary Fibrosis (IPF), a progressive disorder that usually affects individuals over 55 years of age and is manifested histopathologically by the Usual Interstitial Pneumonitis (UIP) pattern characterized by variable degrees of inflammation, honeycomb cysts, distortion of the lung architecture, fibroblastic foci, fibrosis, and marked spatial heterogeneity; Raghu G, Collard H R, Egan J J, et al. *An official ATS/ERS/JRS/ALAT statement: idiopathic pudmonary fibrosis: evidence-based guidelines for diagnosis and management.* American journal ofrespiratory and critical care medicine 2011; 183:788-824. Because of the lack of effective treatments and the rapid progression to respiratory failure and death, IPF remains one of the leading indications for lung transplantations worldwide; Rahu, et al., id.; Yusen R D, Christie J D, Edwards L B, et al. The Registry of the International Society for Heart and Lung Transplantation: Thirtieth Adult Lung and Heart-Lung Transplant Report-2013; focus theme: age. The Journal of heart and lung transplantation: the official publication of the International Society for Heart Transplantation 2013; 32:965-78. Several environmental risk factors have been implicated in the pathogenesis of IPF including cigarette smoking and chronic aspiration (Rahu, et al., id), and a genetic predisposition has been demonstrated (Marshall R P, McAnulty R J, Laurent G J. *The pathogenesis of pulmonary fibrosis: is there a fibrosis gene*? The International Journal of Biochemistry & Cell Biology 1997; 29:107-20), however, the great majority of cases of IPF are sporadic.

The pathogenesis of IPF remains poorly understood and progress is impaired by the lack of an animal model that recapitulates the salient features of the human disease. Recently identified kindreds with ILD developing in multiple members have provided potential clues to the pathogenesis of IPF occurring in the general population; Kropski J A, Lawson W E, Young L R, Blackwell T S. *Genetic studies provide clues on the pathogenesis of idiopathic pulmonary fibrosis.* Disease models & mechanisms 2013; 6:9-17. Familial Pulmonary Fibrosis (FPF), defined as idiopathic interstitial lung disease in two or more first-degree relatives (parent, sibling, or offspring), has been attributed to nonsynonymous mutations in surfactant protein A2 (SFTPA2), surfactant protein C (SFTPC) and ATP-binding cassette A3 (ABCA3)(Lawson W E, Grant S W, Ambrosini V, et al. *Genetic mutations in surfactant protein C are a rare cause of sporadic cases of IPF.* Thorax 2004; 59:977-80; Wang Y, Kuan P J, Xing C, et al. *Genetic defects in surfactant protein A2 are associated with pulmonary fibrosis and lung cancer.* American Journal of Human Genetics 2009; 84:52-9), and to a common variant in the promoter of the gene encoding mucin 5B (MUC5B) that increases MUC5B expression by 37.4-fold; Seibold M A, Wise A L, Speer M C, et al. *A common MUC5B promoter polymorphism and pulmonary fibrosis.* The New England Journal of Medicine 2011, 364:1503-12.

These mutations are proposed to converge on activation of the unfolded protein response; Kropski, J A, et al., 2013, id. A plurality of FPF kindreds, ~15%, have mutations in the telomerase genes, TERT and TERC, and exhibit shortened telomeres; Tsakiri K D, Cronkhite J T, Kuan P J, et al. *Adult-onset pulmonary fibrosis caused by mutations in telomerase.* Proceedings of the National Academy of Sciences of the United States of America 2007; 104:7552-7; Armanios M Y, Chen J J, Cogan J D, et al. *Telomerase mutations in families with idiopathic pulmonary fibrosis.* The New England Journal of Medicine 2007; 356:1317-26. Telomere shortening is also evident in 25% of patients with sporadic IPF who do not have identifiable mutations in TERT or TFRC; Cronkhite J T, Xing C, Raghu G, et al. *Telomere shortening in familial and sporadic pulmonary fibrosis.* American Journal of Respiratory and Critical Care Medicine 2008; 178:729-37.

Despite these advances, the pathogenesis of sporadic IPF remains unclear. Accordingly it is one object of the inventors to identify and describe herein a new mutation segregating in three siblings with pulmonary fibrosis in the calcium binding protein gene, S100A3 (NM_002960). The mutation leads to lower expression of the S100A3 protein and is associated with aberrant intracellular calcium homeostasis and reduced capacity to tolerate oxidative stress in isolated cells. These results indicate that S100A3 regulates pulmonary fibrosis and restoration of S100A3 protein levels that may reverse the clinical symptoms and provide a new therapy for the disease. It is a further object of the present disclosure to provide a method for determining mitigating and/or reducing a risk of fibrosis.

BRIEF SUMMARY OF THE INVENTION

The invention involves treatment of lung fibrosis and respiratory failure using S100A3 protein in subjects that lack functional S100A3 protein, such as a homozygous subject carrying missense variant rs138355706, (229C>T). As shown herein the inventors identified a homozygous variant in a previously unreported gene coding for the calcium binding protein S100A3, segregating in the 3 patients afflicted and 13 additional family members who were either heterozygous carriers or wild-type normal for the variant. Indirect immunofluorescence and Western blots demonstrated decreased expression of the protein in the lungs of patients and in cells isolated from the patient's skin. This was concomitant with aberrant calcium homeostasis in isolated patient's fibroblasts. The introduction of wild type gene in the patient's cells restored their normal calcium responses. Furthermore, the introduction of the mutant transcript caused aberrant calcium homeostasis that was similar to that of seen in patient's cells.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1A. The pedigree of Family 1A with haplotype and genotype analyses; disease haplotype is highlighted in yellow (or *). Genotype of variants in genes S100A3: c.229 C>T transition (rs138355706) causing p.R77C is denoted in red text (or see lines designated by arrows).

FIG. 1B shows linkage analysis resulting in a peak where the maximum multipoint LOD score was 5.28 corresponding to chromosome 1p12-q21.3.

FIG. 1C shows a single ROH as a result of homozygosity mapping shared by all affected patients between rs10802117 and rs11808053 confirming linkage analysis.

FIG. 1D. Shows the sequence chromatogram indicating the wild-type, homozygous affected and heterozygous carrier forms of the C to T transition at position c.229 changing arginine residue to cysteine at position 77 of the S100A3 protein (c.229C>T, p.R77C). Mutation name is based on the full-length S100A3 transcripts.

FIG. 3A. Calcium response of skin fibroblasts (isolated from control; upper green line; and patients; lower red line) to stimulation by fibroblast growth factor (FGF) added at the first arrow. Second arrow depicts the time of addition of the calcium ionophore ionomycin and the third arrow indicates the time of addition of EGTA.

FIG. 3B. Calcium response of skin fibroblasts (isolated from control: upper blue line; and patients; lower red line) to stimulation by bradykinin.

FIG. 3C. Maximum calcium responses to ionomycin in control, patients, patient cells transfected with wildtype transcript of S100A3 (rescued) and control cells transfected with mutant S100A3 transcript (mutant).

DETAILED DESCRIPTION OF THE INVENTION

Figure 2A:
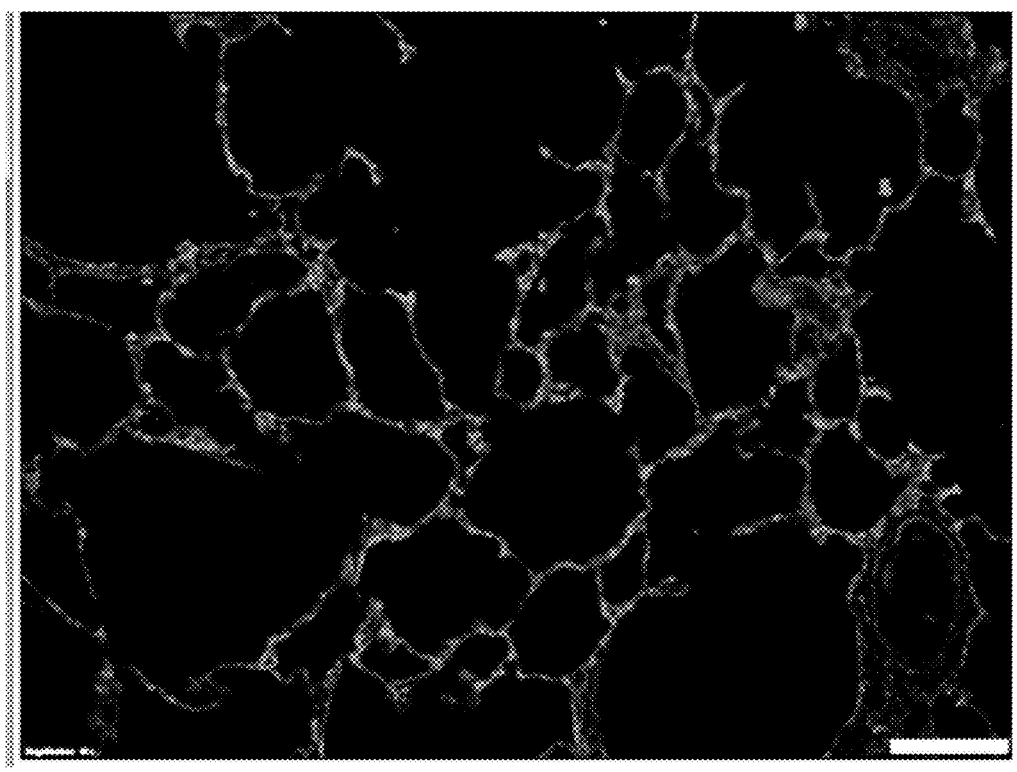
FIGS. 2A and 2B. Immunofluorescence micrographs demonstrating reduced expression of S100A3 protein levels in normal (FIG. 2A) and patients lung tissues (FIG. 2B).
Figure 2B:
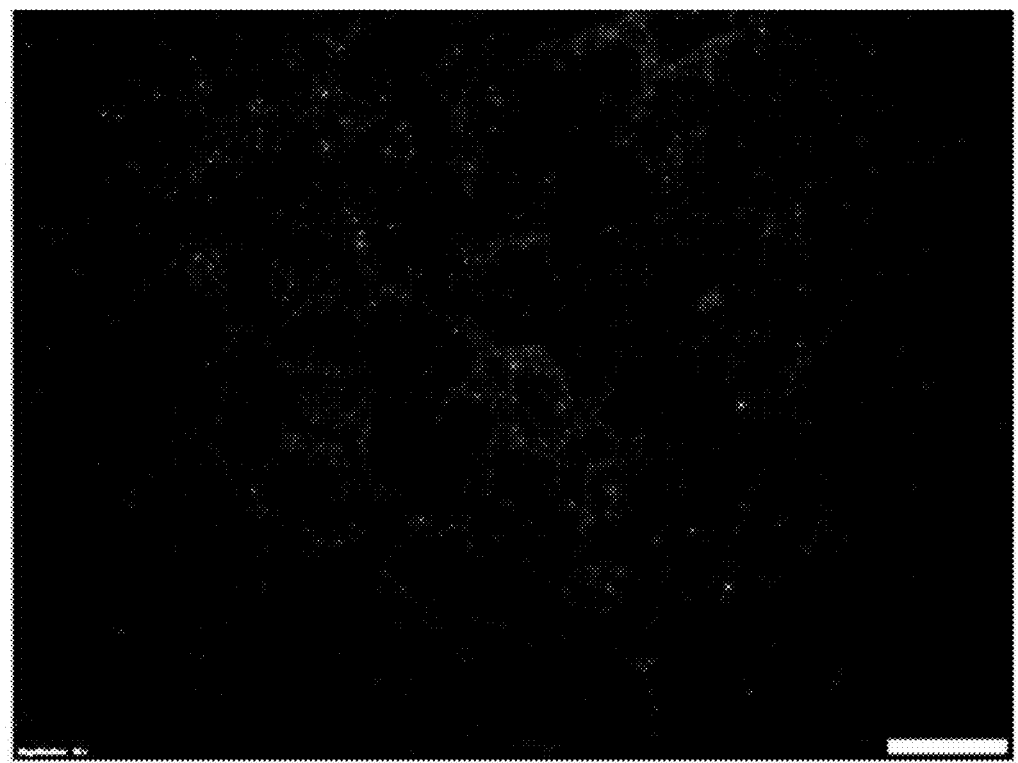

Embodiments of the present disclosure will now be described more fully hereinafter with reference to the accompanying drawings, in which some, but not all embodiments of the disclosure are shown.

The term S100A3 polypeptide describes a class of polypeptides that typically have about 70, 75, 80, 85, 90, 95, 96, 97, 98, 99, <100 or 100% sequence identity or similarity to SEQ ID NO: 2. This class includes a wild-type, functional S100A3 polypeptide of SEQ ID NO: 2 and other functional natural variants as well as a non-functional mutant S100A3 polypeptide of SEQ ID NO. 4. A mutant S100A3 protein will have a non-wild-type amino acid sequence, and typically exhibit aberrant expression, folding and/or activity compared to wild-type S100A3 protein. One example of such a mutant S100A3 protein is described by SEQ ID NO: 4 which contains the p.R77C point mutation.

BLASTN may be used to identify a polynucleotide sequence having at least 70, 75, 80, 85, 90, 95, 96, 97, 98, 99, <100, or and 100% (or any intermediate %) sequence identity to a reference polynucleotide. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered/masked. Default settings are described by and incorporated by reference to <hypertext transfer protocol://blast.ncbi.nlm.nih.gov/Blast.cgi?PROGRAM=blastn&BLAST_ PROGRAMS=megaBlast&PA GE_TYPE=BlastSearch&SHOW_DEFAULTS=on&LINK_LOC=blasthome> (last accessed Sep. 10, 2018).

BLASTP can be used to identify an amino acid sequence having at least 70%, 75%, 80%, 85%, 87.5%, 90%, 92.5%, 95%, 96, 97.5%, 98%, 99%, <100% or 100% (or any intermediate %) sequence identity or similarity to a reference amino acid using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Default settings for BLASTP are described by and incorporated by reference to <hypertext transfer protocol://blast.ncbi.nlm.nih.gov/Blast.cgi?PROGRAM=blastp&PAGE_TYPE=BlastSearch&LINK_LOC=blasthome> (last accessed Sep. 10, 2018).

The term "S100A3 polypeptide" also includes functional fragments of S100A3 which exert at least one biological, physiological or immunological activity or function of a wild-type S100A3 polypeptide. A fragment may contain up to 5, 10, 15, 20, 30, 40, 50, 60, 70, 80, 90, 95, 96, 97, 98, 99 or <100% of the residues of a native or variant S100A3 polypeptide.

A S100A3 polypeptide, variant or fragment thereof may be produced by methods known in the art including by cloning and recombinant expression in a host cell or by chemical synthesis. Many protein expression and purification systems are known and incorporated by reference to <hypertext transfer protocol secure://_en.wikipedia.org/wiki/Protein_production> (last accessed Sep. 10, 2018).

A S100A3 polyrucleotide is one that encodes S100A3 protein or a functional fragment thereof as well as naturally occurring polymorphs or mutants thereof. Variant S1001A3 polynucleotides have sequences that are at least 5, 10, 15, 20, 30, 40, 50, 60, 70, 80, 90, 95, 96, 97, 98, 99 or <100% identical to those of SEQ ID NOS: 1 or 3. Examples include the wild-type polynucleotide described by SEQ ID NO: 1 and a mutant S100A3 polynucleotide of SEQ ID NO: 3 identified by the inventors. A polymorph or variant may have 1, 2, 3, 4, 5, or more nucleotide deletions, substitutions or insertions compared to a naturally occurring S100A3 polynucleotide.

Single nucleotide polymorphisms and other polymorphisms. A polymorphism in an S100A3 polypeptide may be detected or analyzed by methods known in the art, including by methods using the polymerase chain reaction, DNA sequencing, capillary electrophoresis, mass spectrometry; single-strand conformation polymorphism (SSCP); single-base extension; electrochemical analysis; denaturating HPLC and gel electrophoresis; restriction fragment length polymorphism; or hybridization analysis. Typically, the polymorphism will occur in a coding region for the S100A3 protein, such as a missense mutation causing an amino acid residue substitution, but a polymorphism may also occur outside of the coding region, for example, in a flanking DNA sequence.

Homozygous affected subjects typically have two copies of a non-functional mutant S100A3 gene.

Heterozygous carriers. Some individuals have one wild-type S100A3 gene and one mutant S100A3 gene and thus are heterozygous for this gene. Carrying a single copy of the nonfunctional mutant gene may cause altered responses to certain physiological stimuli and negatively impact lung function, especially lower lung functions including compromising lung reserve.

Treatments include administering functional S100A3 protein to a subject deficient in or totally lacking functional S100A3 protein. As shown herein the effects of a mutation in S100A3 on cellular responses can be reversed by administration of functional, wild-type S100A3 protein.

Functional S100A3 protein may be administered systemically and/or locally, preferably directly or indirectly into the respiratory system. Functional S100A3 protein may be administered into the lungs using a nebulizer or metered dose inhaler to rectify abnormal cellular responses or halt the progression of lung fibrosis. Functional S100A3 protein and other active ingredients, such as antibodies that selectively bind to non-functional S100A3 protein, are preferably prepared in a form that can reach and persist in target respiratory tissues such as the lungs, bronchi and other airways.

A pulmonary route of administration offers many advantages including noninvasive delivery of protein and peptide-based drugs, absorption of a drug through the lungs by simple diffusion and carrier-mediated transport, often a decrease in the amount of drug to be administered, fast adsorption and better patient compliance that other parenteral routes.

However, functional S100A3 protein, or other active ingredients like antibodies that bind to and remove non-functional, mutant S100A3 protein, may be administered by other routes including intravenously, intraperitoneally, subcutaneously, intramuscularly, and topically.

Oral administration may be contemplated so long as the functional S100A3 protein is administered in a form that is not digested prior to reaching a target site or being adsorbed into the body.

A nebulizer is a drug delivery device that administered a drug, such as functional S100A3 or antibodies that bind to non-functional or other medicaments in an inhalable form. Nebulizers for treatment of cystic fibrosis, asthma, COPD and other respiratory diseases are known and incorporated by reference to <hypertext transfer protocol secure://en.wikipedia.org/wiki/Nebulizer>. These include soft mist inhalers, jet nebulizers, ultrasonic wave nebulizers, and nebulizers using vibrating mesh technology.

A metered-dosage inhaler is another drug delivery device that delivers a selected or metered amount of a medication, such as functional S100A3 protein or an antibody that binds to non-functional or mutant S100A3 protein. Typically, this device produces and releases an aerosol of micrometer-sized particles that are inhaled. In some cases, the particles may be a dry powder in others as a mist or in a semiliquid form. Metered-dose inhalers and their various components, propellants, excipients and other elements are described by and incorporated by reference to <hypertext transfer protocol secure://en.wikipedia.org/wiki/Metered-dose_inhaler>. An inhalable composition may be formulated in the form of a hydrofluoroalkane inhaler or HFA (metered dose inhaler or MDI), dry powder inhaler (DPI), or as a nebulizer solution.

Functional S100A3 protein or antibodies that bind to non-functional S100A3 protein or other medicaments may be administered as a bolus, or over a period of time, such as at 0.25, 0.5, 1, 2, 3, 4, 5 or more hour intervals. Dosages of functional S100A3 protein may range from 1, 2, 5, 10, 20, 50, 100, 200, 500 or more picomoles to 1, 2, 5, 10, 20, 50, 100, 200, 500 or more millimoles.

Modes of administration for functional S100A3 or other active ingredients of the invention include by nebulizer, oral, sublingual, rectal, topical, parenteral (other than IV and IM), intravenous injection, intramuscular injection and intraperitoneally. Injection of DNA encoding a functional S100A3 protein may also be used as well as gene therapy of cells, such as by transformation of pulmonary cells with a nucleic acid encoding functional S100A3 protein Intravenous administration delivers a drug, such as functional S100A3 protein or an antibody that binds to nonfunctional S100A3 protein directly into a vein. It is usually considered one of the fastest ways to deliver a drug. A drug may be administered as a bolus, for example, by i.v. push or by injection with a syringe, or by continuous infusion over a period of 0.0.25, 0.5, 1, 2, 3, 4, 5 or more hours.

Antibody-based treatments include administration of antibodies that selectively bind to non-functional S100A3 protein and inactivate, promote its removal, or remove it so that subsequently administered wild-type or functional S100A3 protein may exert a therapeutic function by replacing non-functional S100A3 protein. Antibodies that selectively bind to mutant S100A3 protein, but have a lower or no binding affinity for wild-type or functional S100A3 protein may be administered systemically or locally, including into the respiratory system. These may be administered before, at the same time as, or after administration of a functional S100A3 protein. In some embodiments, an antibody that binds to both functional S100A3 protein as well as to a non-functional mutant S100A3 protein may be pre-administered and after a time sufficient for removal or reduction of non-functional S100A3 protein levels by followed by administration of a functional S100A3 protein.

An antibody may be polyclonal, monospecific, or monoclonal, preferably monoclonal for purposes of uniformity and standardization. Antibodies include IgA, IgE, IgG and IgM as well as their various subclasses. Secretory antibodies, such as sIgA or pentameric IgM may be used. Antibody fragments or antibody conjugates that retain an ability to recognize and bind to non-functional S100A3 protein may also be used.

Compositions. A functional S100A3 protein or other active ingredient of the invention may be formulated as a pharmaceutically acceptable composition, for example, with a physiologically acceptable carrier for pulmonary or intravenous administration. As used herein, a "composition" refers to a mixture of the active ingredient with at least one other chemical component, such as a pharmaceutically acceptable carrier or excipient. One purpose of a composition is to facilitate administration of a functional S100A3 protein or other active ingredients of the invention to a subject.

Depending on the intended mode of administration, the composition can be in the form of solid, semi-solid, liquid, or aerosol dosage forms, such as solutions, powders, tablets, suppositories, pills, capsules, powders, liquids, or suspensions, preferably in unit dosage form suitable for single administration of a precise dosage.

The phrase "pharmaceutically acceptable" as used herein refers to compounds, counterions, materials, compositions, and/or dosage forms which are, within the scope of sound medical judgment, suitable for use in contact with the tissues of human beings without excessive toxicity, irritation, allergic response, or other problem or complication and commensurate with a reasonable benefit/risk ratio. A composition is typically a combination of an active ingredient with a carrier or excipient, inert or active, making the composition especially suitable for diagnostic or therapeutic use in vivo, ex vivo, or in vitro.

The term active ingredient, as used herein, refers to an ingredient in the composition that is biologically active, for example a functional S100A3 protein, antibody that binds to non-functional or mutant S100A3 protein or polynucleotide encoding these proteins. Other active ingredients include, but are not limited to, those that exert a substantial pharmacokinetic or pharmacodynamic activity when in admixture with the active ingredients of the invention, for example, other excipients, buffers, or stabilizers, or other drugs approved for administration to the respiratory system.

As used herein, a pharmaceutically acceptable carrier refers to a carrier or diluent that does not cause significant irritation to an organism, does not abrogate the biological activity and properties of the administered active ingredient, and/or does not interact in a deleterious manner with the other components of the composition in which it is contained.

The term carrier encompasses any excipient, binder, diluent, filler, salt, buffer, solubilizer, lipid, stabilizer, or other material well known in the art for use in pharmaceutical formulations, for example, for intravenous administration a carrier may be sodium chloride 0.9% or mixtures of normal saline with glucose or mannose. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid or tocopherol; low molecular weight polypeptides having 2, 3, 4, 5, 6, 7, 8, 9, 10 or fewer residues; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS® (BASF; Florham Park, N.J.).

In some embodiments an active ingredient of the invention, such as functional S100A3 protein may be administered in a carrier used to administer other drugs to the respiratory system, such as carriers for anti-inflammatory drugs. It may also be administered in combination with an anti-inflammatory drug such as an inhaled steroid such as Beclomethasone dipropionate(Qvar), Budesonide (Pulmicort), Budesonide/Formoterol(Symbicort)—a combination drug that includes a steroid and a long-acting bronchodilator drug, Fluticasone (Flovent), Fluticasone inh powder(Arnuity Ellipta), Fluticasone/Salmeterol (Advair)—a combination drug that includes a steroid and a long-actingbronchodilator drug, Mometasone (Asmanex), or Mometasone/formoterol (Dulera)—a combination drug that also includes a long-acting bronchodilator drug. In some embodiments one or more NSAIDs may be adminstered as additional active ingredients, these include aspirin, celecoxib (Celebrex), diclofenac (Cambia, Cataflam, Voltaren-X R, Zipsor, Zorvolex), diflunisal (Dolobid), etodolac, ibuprofen (Motrin, Advil), indomethacin (Indocin), ketoprofen, ketorolac (Toradol), nabumetone, naproxen (Aleve, Anaprox, Naprelan, Naprosyn, oxaprozin (Daypro), piroxicam (Feldene), salsalate (Disalsate), sulindac) or tolmetin. A secondary active ingredient may be administered by the same or by a different route or mode of administration.

For therapeutic purposes, formulations for parenteral administration can be in the form of aqueous or non-aqueous isotonic sterile injection solutions or suspensions. The term parenteral, as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration, preferably in a digestion-resistant form such as an enteric coating. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

DNA- or RNA-based vaccines. In some embodiments, DNA encoding an S100A3 protein of the invention may be replicated or synthesized by known methods. The DNA is then formulated for administration to a subject, for example, by pulmonary, intravenous, subcutaneous, intramuscular, intrapulmonary, or intralymphatic administration. DNA-based vaccines and methods of their use are known and are incorporated by reference to Tregoning, J S, et al., *Using Plasmids as DNA Vaccines for Infectious Diseases*. Microbiol Spectr. 2014 December; 2(6). doi: 10.1128/microbiolspec.PLAS-0028-2014; Ramirez, L A, et al., *Therapeutic and prophylactic DNA vaccines for HIV*-1. Expert Opin Biol Ther. 2013 April; 13(4):563-73. doi: 10.1517/14712598.2013.758709; Williams, JA, *Improving DNA vaccine performance through vector design*. Curr Gene Ther. 2014; 14(3):170-89.

In some embodiments, mRNA encoding a S100A3 polypeptide of the invention may be produced by transcribing or otherwise producing an RNA molecule corresponding to DNA encoding the polypeptide by known methods. The RNA is then formulated for administration to a subject, for example, by intravenous, subcutaneous, intramuscular, intrapulmonary, or intralymphatic administration. RNA-based vaccines and methods of using them to induce immunity are described by and incorporated by reference to Hubaud, A., RNA vaccines: a novel technology to prevent and treat disease, <hypertext transfer protocol://_sitn.hms.harvard.edu/flash/2015/ma-vaccines-a-novel-technology-to-prevent-and-treat-disease/> and to Pardi, N., et al., mRNA vaccines—a new era in vaccinology Nat Rev Drug Discov. 2018 April; 17(4):261-279. doi: 10.1038/nn:d.2017.243. Epub 2018 Jan. 12.

Other active ingredients. In some embodiments, other active ingredients in addition to a functional S100A3 protein or polynucleotide encoding it, or to an antibody or antibody fragment that binds to non-functional S100A3 protein may be incorporated into a composition or separately administered in conjunction with at least one active ingredient of the invention. These include anti-inflammatory agents, colchicine, corticosteroids, including inhalable corticosteroids like flunisolide fluticasone furoate fluticasone propionate-triamcinolone acetonide beclomethasone dipropionate and Budesonide; immunosuppressants such as cyclophosphamide, azathioprine, methotrexate, penicillamine, and cyclosporine, or cytokines, such as IFN-gamma.

Protease inhibitors may be administered to increase the biological life of functional S100A3 protein or other active ingredients of the invention or otherwise inhibit protease activity during treatment; see <hypertext transfer protocol secure://www.ddw-online.com/therapeutics/pI48402-protease-inhibitor-therapeutics-for-respiratory-disease-winter-03.html>, last accessed Sep. 10, 2018, incorporated by reference).

In some embodiments, one or more chaperonins may be administered to correct protein misfolding, along with an active component of the invention such as along with a functional S100A3 protein. Chaperonins are incorporated by reference to Elena L. Rudashevskaya, Thomas Stockner, Michael Trauner, Michael Freissmuth and Peter Chiba. *Pharmacological correction of misfolding of ABC proteins*. Drug Discov Today Technol. 2014 June; 12(100): e87-e94. doi: 10.1016/j.ddtec.2014.03.009. PMCID: PMC4039138 PMID: 25027379. In another embodiment, the mutant S100A3 proteins described herein may be used as targets for screening of chaperonin compounds that increase or restore wild-type S100A3 functionality. Such a method would involve contacting a mutant S100A3 protein or a cell expressing it with a chaperonin, detecting an increase in at least one wild-type S100A3 activity, and, optionally, treating a subject who expresses a mutant S100A3 protein with a chaperonin that increases the wild-type activity.

Antioxidants, such as ascorbates or tocopherols may be administered as well as oxygen before, during or after therapy with an active ingredient of the invention.

Improvement in status of pulmonary fibrosis may be determined by CT scanning to show general fibrosis and staging according to CT results and lung function tests. Improvement is measured by halting the progress of the disease or by reducing the already existing fibrosis which can be determined using CT scans and lung functional tests.

Other, non-limiting embodiments of the invention include those described below.

A method for determining a risk of fibrosis comprising detecting a mutant S100A3 protein or a mutant polynucleotide encoding it in a biological sample from a subject, and, optionally, treating the subject to reduce a risk of fibrosis or treating the subject for fibrosis. This method may include detecting the mutant S100A3 protein and wherein the mutant S100A3 protein comprises an amino acid residue that is not arginine at position 77; include detecting the mutant S100A3 protein and wherein the mutant S100A3 protein comprises an amino acid residue that is cysteine at position 77; detecting a mutant S100A3 protein and the mutant S100A3 protein comprises the amino acid sequence described by SEQ ID NO: 4; or detecting a mutant S100A3 protein by contacting it with an antibody that selectively binds to the mutant S100A3 protein in comparison to a not mutated S100A3 protein.

An antibody to a mutant S100A3 protein, such as one that binds to S100A3 (SEQ ID NO: 4) carrying the p.R77C mutation, will preferably have a higher affinity or avidity for the mutant S100A3 protein than for the wild-type protein, more preferably, will bind to the mutant S100A3 protein but will substantially not bind to the wild-type S100A3 protein.

Linear B cell epitopes of a mutant S100A3 protein will typically contain one or more mutations to the wild-type amino acid sequence, for example, the p.R77C mutation shown by SEQ ID NO: 4. In some instances, a mutation will be part of, of form by its allosteric effects, a conformational epitope that can be used to distinguish a wild-type S100A3 protein from a mutant S100A3 protein. B cell epitopes typically contain about 5 to 20 amino acid residues Those skilled in the art can identify B cell epitopes by methods known in the art including those described by El-Manzalawy Y, et al., Comput Syst Bioinformatics Conf. 2008; 7: 121-132. A B cell epitope on a mutant S100A3 protein may span 5, 6, 7, 8, 9, 10, 11, 12, 13, 14, 15, 16, 17, 18, 19 or 20 amino acid residues of SEQ ID NO: 4 and contain the p.R77C mutation or another mutation to residue 77 (or other residues) of wild-type S100A3 protein. Peptides having B cell epitopes may be used to produce polyclonal or monoclonal antibodies to a mutant S100A3 protein by methods known in the art including those described by or cited to by <hypertext transfer protocol secure://en.wikipedia.org/wiki/Monoclonal_antibody> (incorporated by reference, last accessed Sep. 23, 2018).

In other embodiment this method may include detecting a polynucleotide encoding a mutant S100A3 protein and wherein the mutant S100A3 protein comprises an amino acid residue that is not arginine at position 77; detecting a polynucleotide encoding a mutant S100A3 protein and wherein the mutant S100A3 protein comprises an amino acid residue that is cysteine at position 77; detecting a polynucleotide encoding a mutant S100A3 protein that comprises the amino acid sequence described by SEQ ID NO: 4; detecting a polynucleotide comprising rs138355706 (229C>T); or detecting a polynucleotide that encodes the mutant S100A3 protein using probes and/or primers that selectively recognize the polynucleotide comprising rs138355706 (229C>T). Primers that amplify a polynucleotide encoding a mutant S100A3 protein may be designed by methods known in the art, such as those disclosed by Primer-BLAST available at <hypertext transfer protocol secure://www.ncbi.nlm.nih.gov/tools/primer-blast> (incorporated by reference, last accessed Sep. 23, 2018). Primers and probes that identify polynucleotides encoding mutant S100A3 proteins may also be designed using tools such as OligoArchitect™ tool available from Sigma-Aldrich and incorporated by reference to <hypertext transfer protocol secure://www.sigmaaldrich.com/technical-documents/articles/biology/oligoarchitect-online.html> (last accessed Sep. 23, 2018). Those skilled in the art can design primers and probes for amplification and/or detection of polynucleotides encoding S100A3 mutant polypeptides using these tools and then select primers that preferentially amplify or hybridize to polynucleotides encoding mutant S100A3 protein in comparison to those encoding the wild-type S100A3 protein. One embodiment of primers or probes of the invention encompasses any primer or probe that can detect the c.229C>T substitution as shown in SEQ ID NO: 3 in any order.

The method may further include detecting whether the subject is homozygous for a polynucleotide encoding a mutant S100A3 protein, heterozygous for a polynucleotide encoding a mutant S100A3 protein, or whether the subject is homozygous for a gene encoding a not mutated S100A3 protein. In some embodiments, the method may involve determining a pedigree or degree of relationship for a heterozygous or homozygous subject.

The method may involve treating a fibrosis, including organ fibrosis or pulmonary fibrosis.

Another embodiment of the invention is directed to a method for reducing the risk of fibrosis or lung disease, or for treating fibrosis or lung disease in a subject who has at least one gene encoding a non-functional mutant S100A3 protein comprising administering to said subject a polynucleotide encoding a functional S100A3 protein, administering a functional S100A3 protein, or administering at least one activator or inhibitor of an S100A3 protein. The subject in this method may be one who has at least one gene comprising a missense mutation rs138355706, (229C>T). In some embodiments, the administering in this method includes administering a polynucleotide encoding a functional S100A3 protein into the respiratory system; administering a functional S100A3 protein into the subject's lungs and further comprises administering an antibody or antibody fragment that specifically binds to the mutant S100A3 polypeptide of SEQ ID NO: 4; or administering at least one activator or inhibitor of S100A3 protein into the subject's lungs.

Another embodiment of the invention is directed to a pharmaceutical composition containing at least one polynucleotide encoding a functional S100A3 protein, at least one functional S100A3 protein, or at least one activator or inhibitor of an S100A3 protein, in an amount sufficient to reduce the severity of fibrosis when administered to a subject in need thereof. Such a composition may be in the form of a dust, aerosol or mist or another form that reaches the lungs or other target site once inhaled.

EXAMPLE

The following Example illustrates various aspects of the present invention. They are not to be construed to limit the claims in any manner whatsoever.

Brief Case Description. Three siblings, two girls and one boy, from a total of seven children were born heathy to consanguineous Saudi Arabian parents after normal pregnancies and deliveries (see chart in FIG. 1A). The parents did not report any medical problems until all three children developed respiratory fibrosis at a young age. All 3 affected siblings had an identical clinical presentation and course. They all developed dyspnea in their early teens and apart from the lung abnormalities, complete and extensive medical examinations revealed normal appearance, development and laboratory findings.

Pulmonary function testing showed severe restriction and impaired oxygen transfer (FIG. 2B) and fibrosis with a non-specific pattern was revealed by chest CT imaging (FIG. 2A). The subjects had extensive medical investigations in Saudi Arabia and the USA, resulting in exclusion of known (including genetic) causes of lung fibrosis. Their respiratory symptoms worsened with age and all 3 patients developed chronic type 2 respiratory failure.

Two of the siblings underwent lung transplantation at ages 22 years and 23 years of age, but died due to primary graft failure. The third sibling died from respiratory failure at 23 years of age. A lung autopsy from one of the subjects revealed nonspecific fibrosis like pattern with microscopic honeycombing (FIG. 1C).

Methods. All subjects provided and institutional review board approved written informed consent (KFSH&RC-RAC #2120 009).

Sequence Analysis. Genomic DNA was extracted from whole blood or paraffin-embedded archived tissue of affected patients, their parents and 11 unaffected relatives using standard methods. Bi-directional exomic sequencing of the coding regions of known IPF-associated genes (TERT, TERC, ABCA3 and SFTPB) was performed in patients and nuclear family members. Sequence analysis was performed manually using the SeqMan 6.1 module of the Lasergene (DNA Star Inc. WI, USA) software package.

Linkage analysis and homozygosity mapping. Linkage analysis was performed using the Allegro module of the easyLINKAGE; Lindner T H, Hoffmann K. *easyLINKAGE: a PERL script for easy and automated two-/multi-point linkage analyses.* Bioinformatics 2005; 21:405-7 (incorporated by reference). This was followed by genotyping on all members using the Affymetrix Axiom@ Genome-Wide CEU 1 Array platform analyzed by homozygosity mapping using AutoSNPa. Direct sequencing of candidate genes in the ROH, linkage interval and exome re-sequencing data of genomic DNA was performed using primer pairs designed to generate overlapping PCR amplicons of the entire coding region of each gene.

Detection of S100A3 message and protein levels. The expression of S100A3 mRNA was performed using RNA isolation kits; TRIzol reagent (Ambion, Grand Island, NY), and complementary DNA was synthesized from 1-5 μg of RNA cDNA kit (Qiagen, Germantown, MD) according to the manufacturer's protocol. Primers for 18S rRNA were purchased from SABiosciences/Qiagen (Valencia, CA). Primers for S100A3 (forward: 5'-cccgaactggtcaactctca (SEQ ID NO: 5); reverse: 5'-gcctggcagagcttgtattt (SEQ ID NO: 6)), and plasmid backbone (forward: 5'-gtggcgctttctcatagctc (SEQ ID NO: 7); reverse: 5'-tgtcttaccgggttggactc (SEQID NO: 8) were designed using PRIMER3. SABiosciences/Qiagen (Valencia, CA). qRT-PCR was performed on an Applied Biosystems StepOne Plus PCR system (Carlsbad, CA) using SYBR Green qRT-PCR Mastermix (SABiosciences) according to the manufacturer's directions. For qRT-PCR of S100A3 in control and patient samples the following primers were used: (forward: 5'-ggaccccgactgagtttcg (SEQ ID NO: 9); reverse: 5'-gctctgaggggcagtccttg (SEQ ID NO: 10). For GAPDH (control for qRT-PCR) the following primers were used (forward: 5'-caccatcttccaggagtgag (SEQ ID NO: 11); reverse: 5'-tcacgccacagtttcccgga (SEQ ID NO: 12)).

Immunofluorescence and western blots were performed using using primary rabbit antibodies against S100A3 purchased from Santa Cruze (Santa Cruze, CA), followed by peroxidase-conjugated goat anti-rabbit IgG (Jackson ImmunoResearch Laboratories; West Grove, PA).

Intracellular calcium and mitochondrial integrity measurements. Intracellular calcium measurements were performed on patient fibroblasts, control fibroblasts (from unaffected donors) transfected with mutant-transcript of S100A3, patients fibroblasts transfected with wild-type S100A3 and control fibroblasts from unaffected individuals as described previously. Receptor mediated changes in intracellular fluorescence intensity in response to FGF (10 ng/ml) and ionomycin (2 μM) were followed using Zeiss LSM 510 META laser scanning confocal system (Carl Zeiss Micro-Imaging, GmbH, Germany). Mitochondria staining were performed using Mito Tracker® Red CMXRos (2 μM, Invitrogen™, Molecular Probes™, USA) and viewed under Zeiss Yokogawa Spinning Disk confocal system (Carl Zeiss MicroImaging, GmbH, Germany).

Identification of a novel IPF region on chromosome 1. Bi-directional exomic sequencing of the candidate familial ILD-associated genes, TERT, TERC, ABCA3 and SFTPB, did not reveal any variations compared to the normal reference sequences in the patients or family members. Subsequent sequence and linkage analysis identified a single peak with a multipoint LOD score of 2.95 corresponding to chromosome 1p12-q23.1 (FIG. 1B). This was confirmed by homozygosity mapping (Carr I M, Flintoff K J, Taylor G R, Markham A F, Bonthron D T. *Interactive visual analysis of SNP data for rapid autozygosity mapping in consanguineous families.* Human Mutation 2006; 27:1041-6, incorporated by reference), which corroborated a single ROH (FIG. 1C) that was shared by all 3 affected patients and not any unaffected family members and included 1579 SNP calls with identical genotypes between rs10802117 and rs1615480 (chr1:120, 127,864-158,944,584 bp: base numbering is according to UCSC Genome Browser, build hg19) spanning approximately 38 Mb containing over 800 annotated genes. Three genes within this region, (MUC1, SMG5, and BCAN) were identified, sequenced and excluded as potential candidate familial ILD-causing genes based on their similarity in function, expression, and/or protein family, type to previously identified familial ILD-associated genes.

Erome sequencing. Whole exome sequencing of all genes in the 31.3 Mbp linkage region was performed in the proband (Individual IV:1 FIG. 1A). After filtering for homozygous non-synonymous SNVs that were either novel or had either low or unknown minor allele frequency in dbSNP, only 3 previously described variants were identified, rs3795737 in ISG20L2, rs143224912 in SETDB1, and rs138355706 in S100A3. Rs3795737 was excluded because it was found in the homozygous state throughout many different populations. Exomic sequencing of SETDB1 and S100A3 was performed in all 3 affected and 6 unaffected family members. The rs143224912 variant in SETDB1 was excluded although it segregated with the disease phenotype, as it was present in 3% of the normal control population samples and due to a complete lack of conservation of the amino acid residue altered by the change throughout all orthologous species. The missense variant rs138355706, (229C>T, missense causing a p.R77C mutation in S100A3) segregated with ILD. All 3 affected patients were homozygous for rs138355706. Both parents were heterozygous for this variant and unaffected siblings and family members and an additional 7 unaffected extended family members were either heterozygous for rs138355706 or were homozygous wild-type (FIG. 1A). In addition, 500 ethnically-matched normal controls were genotyped for this change by re-sequencing of S100A3. Three of these individuals were heterozygous, but none were homozygous for rs138355706, indicating a minor allele frequency of 0.3%. Sequencing of the S100A3 intronic and 5' flanking sequences was performed in the affected patients and no other variants were identified (data not shown).

Haplotype analysis. Haplotype analysis was carried out using 8 markers (4 microsatellite markers flanking S100A3 and 3 further intragenic markers) confirmed that the three affected individuals share a specific disease haplotype on both chromosomes that is not present in the unaffected individuals (FIG. 1C). Similar analysis demonstrated all 3 normal controls that were heterozygous for this change carry the disease haplotype on one chromosome and hence are related to the family therefore excluding them from the normal control set, providing additional support for the S100A3 p.R77C mutation in the pathogenesis of ILD in this family.

Consequences of S100A3 c. 229 C>T mulation. The c.229 C>T mutation results in an arginine to cysteine missense at residue 77 within the second of two EF-hand calcium-binding motifs in the 103 amino acid protein. The predicted consequences of this mutation on protein structure/function was evaluated using the Polyphen-2 (ver. 2.2.2) and SIFT prediction programs. Both programs predicted minor effects of the mutation on protein structure/function with Polyphen-2 and SIFT (version 1.03) scores of 0.004 and 0.21, respectively. Since microRNAs can modify translation efficiency by binding to coding sequence as well as 3'UTR sequence, whether the c.229 C>T mutation altered any known microRNA binding site using MicroSNiPer (release 19) and a minimum 7-nucleotide seed sequence and found no effect of the SNV on predicted microRNA binding sites was analyzed.

Figure 2C:
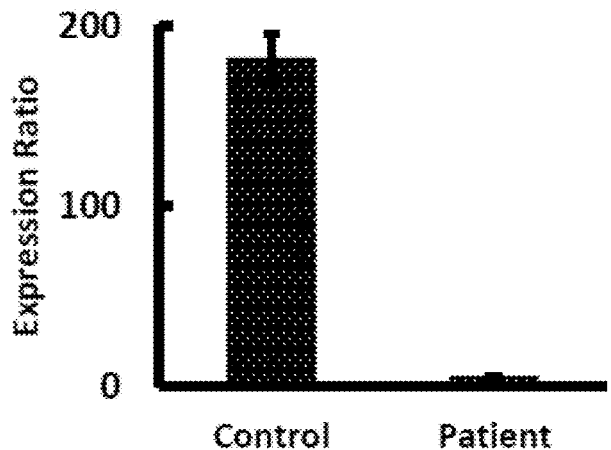
FIG. 2C. Expression of the S100A3 mRNA in control (first bar) and patients cells (second bar) as measured by qtPCR analysis.

Analysis by qRT-PCR demonstrated decreased expression of S100A3 in patients' samples compared to control samples (FIG. 2C).

Figure 2D:
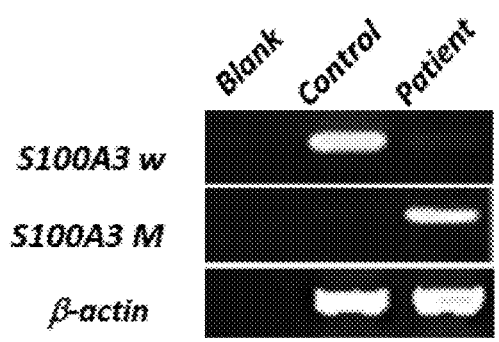
FIG. 2D. Expression of the S100A3 mRNA in control and patients as measured by PCR analysis illustrating the absence of wild type gene in the patient sample and presence of only mutated form of the genes. Beta actin is used as control.

Using qRT-PCR to detect the expression of mutated and control S100A3, it was found that the reduced protein expression was paralleled by reduced mRNA levels for mutant (HEK-M) compared to control S100A3 (HEK-W), see FIG. 2D.

Figure 2E:
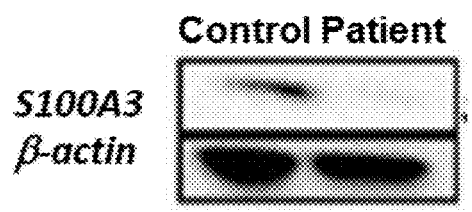
FIG. 2E. Expression of the S100A3 protein in control and patient cells isolated from skin (fibroblasts) using western blot analysis. Beta actin is used as control.
Figure 2F:
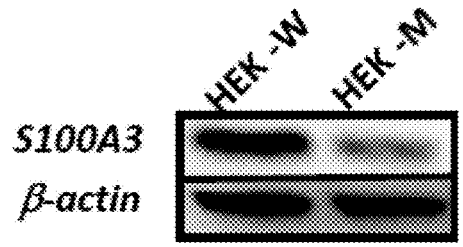
FIG. 2F. Expression of the S100A3 transcripts in human embryonic kidney cells (HEK). Western blot analysis of cells transfected with the wild type S100A3 (HEK-W) and mutant S100A3 (HEK-M). Beta actin is used as control.

Furthermore, the effect of the mutation on the mutant protein expression was confirmed by experiments in which both mutant and wild type S100A3 were HA-tagged and overexpressed in human normal lung fibroblasts. Using anti-HA antibodies to detect S100A3 expression it was found that a consistently reduced mutant S100A3 protein expression at all concentrations of plasmid DNA (FIG. 2E), but similar mRNA levels for wild-type and mutant HA-tagged S100A3 (FIG. 2F).

Effect of S100A3 mutation on intracellular calcium homeostasis and mitochondrial functions. Since the S100 family of protein is calcium binding, the possibility existed that the mutated protein may affect calcium homeostasis.

Figure 3D:
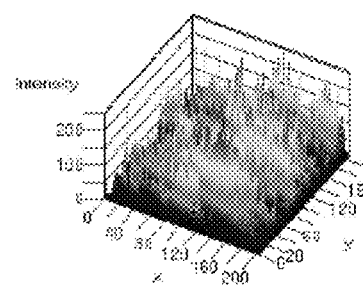
FIGS. 3D and 3E. 3D intensity maps of Mito Tracker® Red CMXRos labelled cells isolated from control (FIG. 3D) and patients (FIG. 3E). Maps are color coded so that warm colors indicate high intensity and cold colors indicate low intensity.

It was found that receptor mediated calcium release was significantly reduced in patients compared to control fibroblast (FIG. 3A).

Furthermore a clear disparity between the levels of ionomycin-induced calcium release in control and patients cells was demonstrated (FIG. 3B).

The effect on intracellular calcium was confirmed in experiments in which patients fibroblasts were transfected with wild type S100A3 transcripts. In this case wild-type S100A3 transcripts significantly restored the ionomycin-induced intracellular calcium levels to that of control levels (FIG. 3C, last bar). Furthermore normal cells transfected with mutant S100A3 exhibited similar calcium homeostasis to that seen in patients' cells (FIG. 3C, third bar).

Figure 3E:
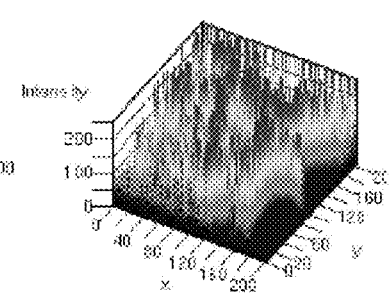

Since the mitochondria are one of the major intracellular calcium stores in many cell types, Mito Tracker® Red CMXRos was used to map possible differences in mitochondrial staining between control and patient's cells. Whereas control cells exhibited the "normal" distinct tubular shapes of mitochondria (FIG. 3D), patients cells exhibited more punctate fluorescence associated with aberrant mitochondrial morphology (FIG. 3E).

Figure 3F:
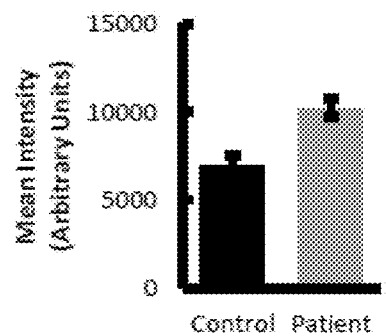
FIG. 3F. Mean fluorescence intensity obtained from flow cytometry of skin fibroblasts isolated from patient and control cells stained with Mitotracker Green.

In addition patient's cells appear to have more mitochondrial staining than control cells (FIG. 3F).

Figure 3G:
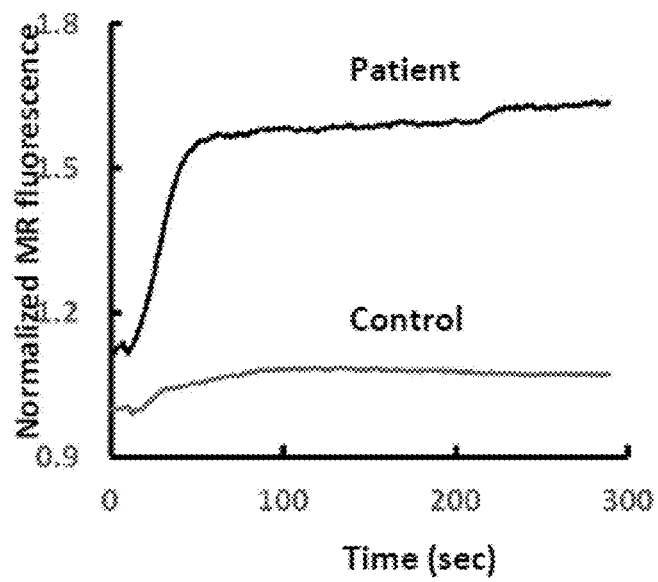
FIG. 3G. Effect of externally added oxidation ($H_2O_2$, 0.03%, arrow) on patients and control cells labeled with Mito Tracker® Red CMXRos.

The integrity of the mitochondria in both patient's and control cells was further investigated by measuring the effect of oxidative stress induced by treating the cells with hydrogen peroxide. FIG. 3G illustrates the ability of control cells to resist oxidative load compared to the patient's cells.

As shown herein, the inventors have identified a novel association for the c. 229C>T (p.R77C) SNV in S100A3 with ILD occurring in three siblings born to consanguineous parents of Saudi Arabian origin. Although p.R77 is classified as a SNP it has not been reported in the heterozygous or homozygous state in the European American population and is only found extremely rarely in the African American population and only in a heterozygous form (Minor allele frequency 0.003%). Further screening and exclusion of this variant in 997 ethnically matched, unrelated healthy control Saudis further confirms its rarity. Further sequencing of the full intronic sequence and 3' untranslated region of S100A3 excluded any other disease-causing variations in the S100A3 gene sequence in the affected family members. The mutation did not alter any predicted microRNA binding sites that could affect protein expression.

S100A3 is a member of the S100 calcium binding proteins and contains two EF-hand calcium-binding domains required for its function; Kizawa K, Uchiwa H, Murakami U. *Highly-expressed S100A3, a calcium-binding protein, in human hair cuticle*. Biochimica et Biophysica Acta 1996: 1312:94-8. The arginine residue altered in the patients is completely conserved among orthologs in five mammalian species and it is located within one of the two EF-calcium binding motifs of the gene, potentially indicating more severe consequences for the protein function than was predicted by the Polyphen-2 and SIFT prediction programs. The missense mutation identified in S100A3 gene in our ILD patients involves a substitution of a positively charged arginine to an uncharged cysteine (p.R77C). Previously, it has been shown that substitution of arginine by alanine at position 77 of S100A3 resulted in a 2.7-fold increase in $Ca^{2+}$ affinity in the mutant protein compared to the wild type; Kizawa K, Takahara H, Troxler H, Kleinert P, Mochida U, Heizmann C W. *Specific citrullination causes assembly of a globular S100A3 homotetramer: a putative Ca2+ modulator matures human hair cuticle*. The Journal of Biological Chemistry 2008; 283:5004-13.

These clinical, molecular and functional results show that S100A3 protein is associated with pathogenesis of lung fibrosis and a good target to which treatments of lung injury may be directed.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page, or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for treating pulmonary fibrosis in a subject carrying missense variant rs13835706 comprising detecting a mutant S100A3 polynucleotide comprising SEQ ID NO: 3 in a biological sample from the subject and administering a therapeutic agent treating the subject for pulmonary fibrosis.

2. The method of claim 1 that comprises detecting a polynucleotide that encodes the mutant S100A3 protein using probes and/or primers that selectively recognize the polynucleotide comprising rs138355706 (229C>T).

3. The method of claim 1, further comprising detecting whether the subject is homozygous for a polynucleotide encoding a mutant S100A3 protein, or heterozygous for a polynucleotide encoding a mutant S100A3 protein.

4. The method of claim 1, wherein said therapeutic agent is an anti-inflammatory drug.

5. The method of claim 1, wherein said therapeutic agent is an inhaled steroid.

6. The method of claim 1, wherein said therapeutic agent is a bronchodilator.

7. The method of claim 1, wherein said therapeutic agent is an NSAID.

* * * * *